(12) United States Patent
Rice et al.

(10) Patent No.: US 11,013,491 B2
(45) Date of Patent: *May 25, 2021

(54) METHOD FOR FOCUSED ACOUSTIC COMPUTED TOMOGRAPHY (FACT)

(71) Applicant: VOLCANO CORPORATION, San Diego, CA (US)

(72) Inventors: Cheryl Rice, San Diego, CA (US); David Sheehan, Poway, CA (US)

(73) Assignee: PHILIPS IMAGE GUIDED THERAPY CORPORATION, San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/054,276

(22) Filed: Aug. 3, 2018

(65) Prior Publication Data
US 2018/0344283 A1 Dec. 6, 2018

Related U.S. Application Data

(63) Continuation of application No. 14/149,569, filed on Jan. 7, 2014, now Pat. No. 10,064,598.
(Continued)

(51) Int. Cl.
*A61B 8/14* (2006.01)
*A61B 8/12* (2006.01)
(Continued)

(52) U.S. Cl.
CPC .............. *A61B 8/14* (2013.01); *A61B 8/0891* (2013.01); *A61B 8/12* (2013.01); *A61B 8/5207* (2013.01);
(Continued)

(58) Field of Classification Search
CPC ....... A61B 8/14; A61B 8/0891; A61B 8/5207; A61B 8/54; A61B 8/12; A61B 8/085;
(Continued)

(56) References Cited

U.S. PATENT DOCUMENTS

| 5,243,988 A | 9/1993 | Sieben et al. |
| 5,546,948 A | 8/1996 | Hamm et al. |

(Continued)

FOREIGN PATENT DOCUMENTS

| DE | 9212636 U1 | 12/1992 |
| EP | 2289420 A1 | 3/2011 |
| WO | 2012136786 A1 | 10/2012 |

OTHER PUBLICATIONS

International Searching Authority/European Patent Office, "Communication—Supplementary European Search Report," for European Application No. 13870540.5, dated Aug. 18, 2016, 7 pages.

(Continued)

*Primary Examiner* — Peter Luong

(57) ABSTRACT

A method for acoustic tomography within a patient may include generating a focused ultrasonic signal using a transducer is provided; the ultrasonic signal forming a path within the patient. The method includes directing the ultrasonic signal on a spot within the patient; scanning the spot in a predetermined pattern about a volume within the patient; receiving an ultrasonic echo in the transducer; converting the ultrasonic echo into a voltage; selecting a frequency band from the voltage; amplifying the voltage in the selected frequency band with a processing circuit; and generating an image of the volume within the patient structure utilizing the amplified voltage. A method for recanalization of a blood vessel including the above acoustic tomography steps is also provided.

14 Claims, 9 Drawing Sheets

Related U.S. Application Data

(60) Provisional application No. 61/750,085, filed on Jan. 8, 2013.

(51) Int. Cl.
*A61B 8/08* (2006.01)
*A61B 8/00* (2006.01)
*A61B 8/06* (2006.01)

(52) U.S. Cl.
CPC .............. *A61B 8/54* (2013.01); *A61B 8/06* (2013.01); *A61B 8/085* (2013.01); *A61B 8/445* (2013.01); *A61B 8/4461* (2013.01); *A61B 8/483* (2013.01); *A61B 8/488* (2013.01)

(58) Field of Classification Search
CPC ......... A61B 8/06; A61B 8/445; A61B 8/4461; A61B 8/483; A61B 8/488
See application file for complete search history.

(56) References Cited

U.S. PATENT DOCUMENTS

| | | | |
|---|---|---|---|
| 5,640,961 A | 6/1997 | Verdonk | |
| 6,013,033 A | 1/2000 | Berger et al. | |
| 6,039,690 A | 3/2000 | Holley et al. | |
| 6,200,268 B1 | 3/2001 | Vince et al. | |
| 6,245,017 B1* | 6/2001 | Hashimoto | A61B 8/06 128/916 |
| 6,544,187 B2 | 4/2003 | Seward | |
| 6,641,540 B2 | 11/2003 | Fleischman et al. | |
| 7,175,597 B2 | 2/2007 | Vince et al. | |
| 7,627,156 B2 | 12/2009 | Margolis et al. | |
| 9,028,414 B2* | 5/2015 | Miyaki | G01S 7/52033 600/442 |
| 2002/0177774 A1 | 11/2002 | Hwang et al. | |
| 2005/0277835 A1 | 12/2005 | Angelsen et al. | |
| 2006/0184023 A1 | 8/2006 | Satoh | |
| 2006/0241465 A1* | 10/2006 | Huennekens | A61B 6/504 600/458 |
| 2007/0016054 A1 | 1/2007 | Cao et al. | |
| 2007/0066888 A1 | 3/2007 | Maschke | |
| 2007/0161897 A1 | 7/2007 | Sasaki et al. | |
| 2007/0260141 A1* | 11/2007 | Margolis | A61B 5/02007 600/437 |
| 2008/0294037 A1 | 11/2008 | Richter | |
| 2009/0030312 A1 | 1/2009 | Hadjicostis | |
| 2009/0131798 A1 | 5/2009 | Minar et al. | |
| 2010/0234736 A1* | 9/2010 | Corl | A61B 8/12 600/463 |
| 2010/0256616 A1 | 10/2010 | Katoh et al. | |
| 2011/0087104 A1 | 4/2011 | Moore et al. | |
| 2011/0232607 A1 | 9/2011 | Yoshioka | |
| 2012/0197113 A1 | 8/2012 | Courtney et al. | |
| 2012/0215091 A1 | 8/2012 | Suzuki et al. | |
| 2012/0220874 A1 | 8/2012 | Hancock et al. | |
| 2012/0271170 A1 | 10/2012 | Emalianov et al. | |
| 2013/0303920 A1 | 11/2013 | Corl | |
| 2014/0066768 A1* | 3/2014 | Sui | G01S 7/52038 600/443 |
| 2014/0187963 A1 | 7/2014 | Corl | |

OTHER PUBLICATIONS

International Search Report and Written Opinion received in Patent Cooperation Treaty Application No. PCT/US2013/076215, dated Apr. 10, 2014, 13 pages.

* cited by examiner

METHOD FOR FOCUSED ACOUSTIC COMPUTED TOMOGRAPHY (FACT)

CROSS-REFERENCE TO RELATED APPLICATION

The present application is a continuation of U.S. application Ser. No. 14/149,569, filed Jan. 7, 2014, which claims the benefit of provisional U.S. Patent Application No. 61/750,085 filed Jan. 8, 2013. The entire disclosure of these applications are incorporated herein by reference.

BACKGROUND

1. Field of the Invention

The present disclosure relates generally to ultrasound imaging inside the living body and, in particular, to a focused intravascular ultrasound (IVUS) imaging catheter that produces high resolution intravascular imaging using a polymer based transducer.

2. Description of Related Art

Intravascular ultrasound (IVUS) imaging is widely used in interventional cardiology as a diagnostic tool for a diseased vessel, such as an artery, within the human body to determine the need for treatment, to guide the intervention, and/or to assess its effectiveness. IVUS imaging uses ultrasound echoes to create an image of the vessel of interest. Ultrasound waves pass easily through most tissues and blood, but they are partially reflected from discontinuities arising from tissue structures (such as the various layers of the vessel wall), red blood cells, and other features of interest. The IVUS imaging system, which is connected to the IVUS catheter by way of a patient interface module (PIM), processes the received ultrasound echoes to produce a cross-sectional image of the vessel where the catheter is placed.

Current IVUS solutions do not provide resolution capable of differentiating structures without significant training in image interpretation. Structures requiring clearer images might include plaque burden, stent apposition, lipid pool identification, thrombus, and stent endothelization. While Optical Coherence Tomography (OCT) devices offer improved resolution, they require flushing to produce the image, and due to limitations of light penetration they do not allow for visualization of the vessel morphology beyond the surface of the vessel. While existing IVUS catheters deliver useful diagnostic information, there is a need for enhanced image quality to provide more valuable insight into the vessel condition. For further improvement in image quality in rotational IVUS, it is desirable to use a transducer with broader bandwidth and to incorporate focusing into the transducer.

What is needed is a method for high resolution ultrasound imaging to assess lesions, characterize vessels or to monitor other structures within a patient's body.

SUMMARY

According to embodiments disclosed herein, a method for acoustic tomography within a patient may include generating a focused ultrasonic signal using a transducer, the ultrasonic signal forming a path within the patient; directing the ultrasonic signal on a spot within the patient; scanning the spot in a predetermined pattern about a volume within the patient; receiving an ultrasonic echo in the transducer; converting the ultrasonic echo into a voltage; selecting a frequency band from the voltage; amplifying the voltage in the selected frequency band with a processing circuit; and generating an image of the volume within the patient structure utilizing the amplified voltage.

Further according to some embodiments, a method for recanalization of a blood vessel may include positioning a flexible member within the blood vessel proximal to a pre-selected area of interest; generating a focused ultrasonic signal using a transducer, the ultrasonic signal forming a path within the blood vessel; directing the ultrasonic signal on a spot within the blood vessel; scanning the spot in a predetermined pattern about a volume within the patient; receiving an ultrasonic echo in the transducer; converting the ultrasonic echo into a voltage; selecting a frequency band from the voltage; amplifying the voltage in the selected frequency band with a processing circuit; and recanalizing a lumen in the blood vessel based on the image.

These and other embodiments of the present invention will be described in further detail below with reference to the following drawings.

BRIEF DESCRIPTION OF THE DRAWINGS

In the figures, elements having the same reference number have the same or similar functions.

DETAILED DESCRIPTION

Figure 1A:
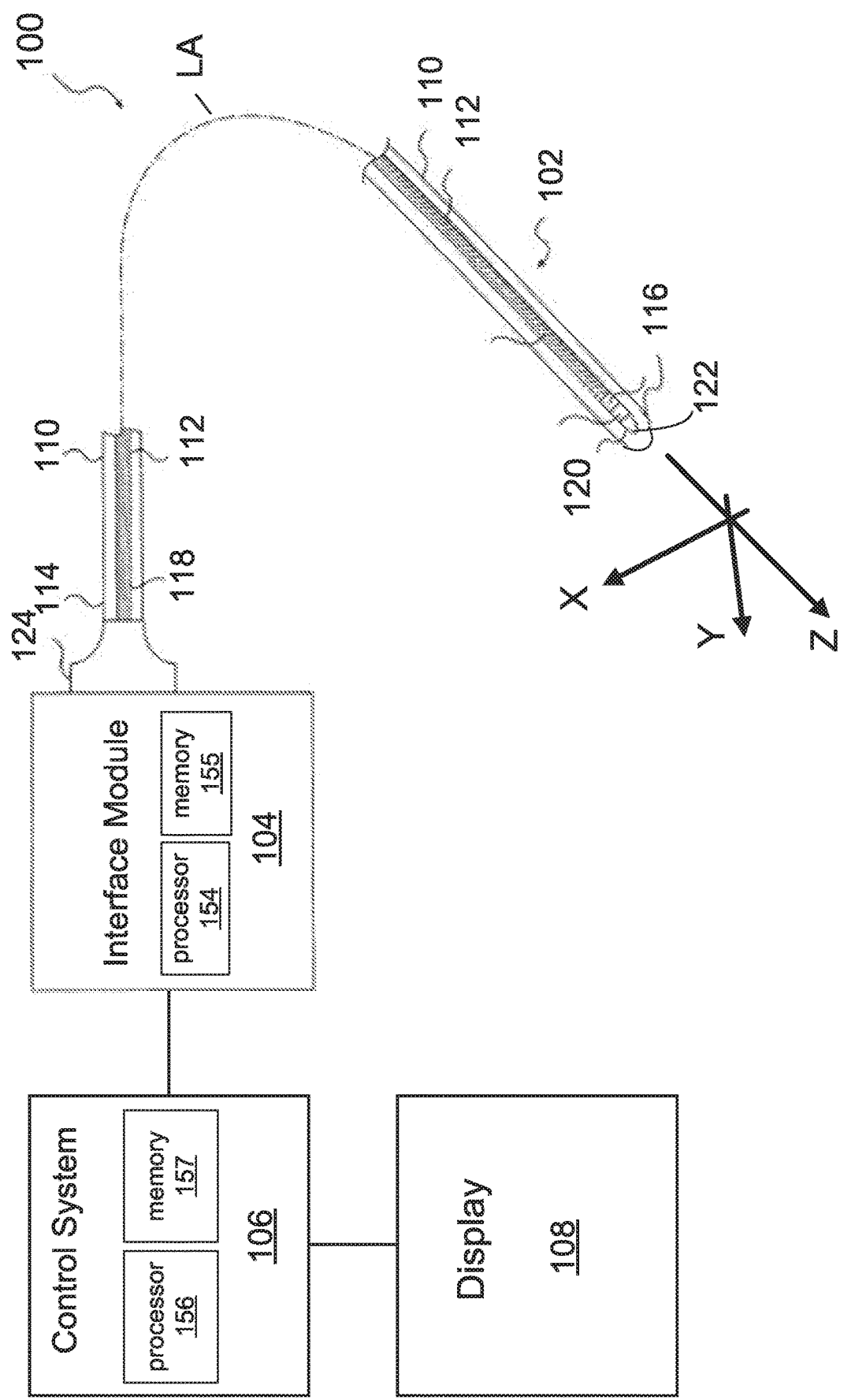
FIG. 1A is a schematic illustration of an intravascular ultrasound (IVUS) imaging system, according to some embodiments.

For the purposes of promoting an understanding of the principles of the present disclosure, reference will now be made to the embodiments illustrated in the drawings, and specific language will be used to describe the same. It is nevertheless understood that no limitation to the scope of the disclosure is intended. Any alterations and further modifications to the described devices, systems, and methods, and any further application of the principles of the present disclosure are fully contemplated and included within the present disclosure as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. For the sake of brevity, however, the numerous iterations of these combinations will not be described separately.

In a typical rotational IVUS catheter, a single ultrasound transducer element is located at the tip of a flexible driveshaft that spins inside a plastic sheath inserted into the vessel of interest. The transducer element is oriented such that the ultrasound beam propagates generally perpendicular to the axis of the catheter. A fluid-filled sheath protects the vessel tissue from the spinning transducer and driveshaft while permitting ultrasound signals to freely propagate from the transducer into the tissue and back. As the driveshaft rotates (typically at 30 revolutions per second), the transducer is periodically excited with a high voltage pulse to emit a short burst of ultrasound. The same transducer then listens for the returning echoes reflected from various tissue structures, and the IVUS imaging system assembles a two dimensional display of the vessel cross-section from a sequence of several hundred of these pulse/acquisition cycles occurring during a single revolution of the transducer. In some embodiments, software may be used to provide reconstruction three-dimensional (3D) images of tissue structures by storing two-dimensional data collected from a rotational IVUS catheter.

In the rotational IVUS catheter, the ultrasound transducer is typically a piezoelectric element with low electrical impedance capable of directly driving an electrical cable connecting the transducer to the imaging system hardware. In this case, a four wire (or quad cable) can be used to carry the transmit pulse from the system to the transducer and to carry the received echo signals from the transducer back to the imaging system by way of a patient interface module ("PIM") where the echo signals can be assembled into an image. To transport the electrical signal across a rotating mechanical junction some embodiments include an electromechanical interface where the electrical signal traverses the rotating junction. In some embodiments of a rotational IVUS imaging system a rotary transformer, slip rings, and rotary capacitors, may be used to create an electrical interface between the PIM and the catheter.

As described in more detail below, ultrasound transducers may be formed to emit a focused beam. Utilizing a focused beam and/or alternate piezoelectric materials allow Focused Acoustic Computed Tomography (FACT) technologies to provide sub 50 µm resolution without compromising depth or penetration. Thereby generating an image which is useful for defining vessel morphology, beyond surface characteristics. Reference will now be made to a particular embodiment of the concepts incorporated into an intravascular ultrasound system. However, the illustrated embodiments and uses thereof are provided as examples only, without limitation on other systems and uses, such as but without limitation, imaging within any vessel, artery, vein, lumen, passage, tissue or organ within the body. Embodiments of focused acoustic computed tomography methods as disclosed herein may also be used for renal denervation applications.

FIG. 1A is a schematic illustration of an intravascular ultrasound (IVUS) imaging system 100, according to some embodiments. IVUS imaging system 100 includes an IVUS catheter 102 coupled by a patient interface module (PIM) 104 to an IVUS control system 106. In some embodiments, a bedside utility box (BUB) or a Bedside Interface Box (BIB) may be used as an interface module. Control system 106 is coupled to a monitor 108 that displays an IVUS image (such as an image generated by the IVUS system 100).

In some embodiments, IVUS catheter 102 is a rotational IVUS catheter, which may be similar to a Revolution® Rotational IVUS Imaging Catheter available from Volcano Corporation and/or rotational IVUS catheters disclosed in U.S. Pat. Nos. 5,243,988 and 5,546,948, both of which are incorporated herein by reference in their entirety, for all purposes. Catheter 102 includes an elongated, flexible catheter sheath 110 (having a proximal end portion 114 and a distal end portion 116) shaped and configured for insertion into a lumen of a blood vessel (not shown). A longitudinal axis LA of the catheter 102 extends between proximal end portion 114 and distal end portion 116. Catheter 102 is flexible such that it can adapt to the curvature of the blood vessel during use. In that regard, the curved configuration illustrated in FIG. 1A is for exemplary purposes and in no way limits the manner in which the catheter 102 may curve in other embodiments. Generally, catheter 102 may be configured to take on any desired straight or arcuate profile when in use.

In some embodiments a rotating imaging core 112 extends within sheath 110. Accordingly, in some embodiments imaging core 112 may be rotated while sheath 110 remains stationary. Imaging core 112 has a proximal end portion 118 disposed within the proximal end portion 114 of sheath 110 and a distal end portion 120 disposed within the distal end portion 116 of sheath 110. Distal end portion 116 of sheath 110 and the distal end portion 120 of imaging core 112 are inserted into the vessel of interest during operation of IVUS imaging system 100. The usable length of catheter 102 (for example, the portion that can be inserted into a patient, specifically the vessel of interest) can be any suitable length and can be varied depending upon the application. The proximal end portion 114 of sheath 110 and the proximal end portion 118 of imaging core 112 are connected to PIM 104. Proximal end portions 114, 118 are fitted with a catheter hub 124 that is removably connected to PIM 104. Catheter hub 124 facilitates and supports a rotational interface that provides electrical and mechanical coupling between catheter 102 and PIM 104.

Distal end portion 120 of imaging core 112 includes a transducer assembly 122. Transducer assembly 122 is configured to be rotated (either by use of a motor or other rotary device) to obtain images of the vessel. Transducer assembly 122 can be of any suitable type for visualizing a vessel and, in particular, a stenosis in a vessel. In the depicted embodiment, transducer assembly 122 includes a piezoelectric micro-machined ultrasonic transducer ("PMUT") and associated circuitry, such as an application-specific integrated circuit (ASIC). An exemplary PMUT used in IVUS catheters may include a polymer piezoelectric membrane, such as that disclosed in U.S. Pat. No. 6,641,540, and co-pending applications entitled "Preparation and Application of a Piezoelectric Film for an Ultrasound Transducer," U.S. Provisional App. No. 61/740,998, filed Dec. 21, 2012, "Focused Rotational IVUS Transducer Using Single Crystal Composite Material," U.S. Provisional App. No. 61/745,425, filed Dec. 21, 2012, and "Transducer Mounting Arrangements and Associated Methods for Rotational Intravascular Ultrasound (IVUS) Devices," U.S. Provisional App. No. 61/747,469, filed Dec. 31, 2012, each hereby incorporated by reference in its entirety. The PMUT may provide greater than about 70% bandwidth, or about 75% bandwidth for optimum resolution in a radial direction, and a spherically-focused aperture for optimum azimuthal and elevation resolution. In some embodiments, a bandwidth of about 75% may be sufficient to obtain high quality images. That is, in some embodiments a transducer assembly fabricated using a PMUT material according to embodiments as disclosed herein may have a response bandwidth that is more than 100% of the center frequency of the response band. For example, if the response band of transducer assembly 122 is 20 MHz, a response bandwidth may be about 20 MHz or more. Thus, the response bandwidth of such transducer assembly may include frequencies from about 10 MHz to about 30 MHz.

Transducer assembly 122 may also include a housing having the PMUT and associated circuitry disposed therein. In some embodiments the housing has an opening that ultrasound signals generated by the PMUT transducer travel through. Alternatively, transducer assembly 122 may include a capacitive micro-machined ultrasonic transducer ("CMUT"). Accordingly, some embodiments may use a flat transducer assembly 122 with an acoustic lens positioned adjacent to the transducer assembly, for beam focusing. In yet another alternative embodiment, transducer assembly 122 could include an ultrasound transducer array (for example, arrays having 16, 32, 64, or 128 elements are utilized in some embodiments) utilizing focus transducer assemblies.

The rotation of imaging core 112 within sheath 110 is controlled by PIM 104. For example, PIM 104 provides user interface controls that can be manipulated by a user. In some embodiments PIM 104 may receive and analyze information received through imaging core 112. It will be appreciated that any suitable functionality, controls, information processing and analysis, and display can be incorporated into PIM 104. Thus, PIM 104 may include a processor circuit 154 and a memory circuit 155 to execute operations on catheter 102 and receive, process, and store data from catheter 102. In some embodiments PIM 104 receives data from ultrasound signals (echoes) detected by imaging core 112 and forwards the received echo data to control system 106. Control system 106 may include a processor circuit 156 and a memory circuit 157 to execute operations on catheter 102 and receive, process, and store data from catheter 102. In some embodiments PIM 104 performs preliminary processing of the echo data prior to transmitting the echo data to control system 106. PIM 104 may perform amplification, filtering, and/or aggregating of the echo data, using processor circuit 154 and memory circuit 155. PIM 104 can also supply high- and low-voltage DC power to support operation of catheter 102 including the circuitry within transducer assembly 122.

In some embodiments, wires associated with IVUS imaging system 100 extend from control system 106 to PIM 104. Thus, signals from control system 106 can be communicated to PIM 104 and/or vice versa. In some embodiments, control system 106 communicates wirelessly with PIM 104. Further according to some embodiments, catheter 102 may communicate wirelessly with PIM 104. Similarly, it is understood that, in some embodiments, wires associated with the IVUS imaging system 100 extend from control system 106 to monitor 108 such that signals from control system 106 can be communicated to monitor 108 and/or vice versa. In some embodiments, control system 106 communicates wirelessly with monitor 108.

The piezoelectric micro-machined ultrasound transducer (PMUT) fabricated using a polymer piezoelectric material, such as disclosed in U.S. Pat. No. 6,641,540 that is hereby incorporated by reference in its entirety, offers greater than about 70% bandwidth, or about 75% bandwidth for optimum resolution in the radial direction, and a spherically-focused aperture for optimum azimuthal and elevation resolution. The electrical impedance of the transducer may be reduced to efficiently drive the electrical cable coupling the transducer to the IVUS imaging system by way of the PIM.

FIG. 1A illustrates a 3-dimensional (3D) Cartesian coordinate system XYZ oriented such that the Z-axis is aligned with the LA. In further descriptions of embodiments disclosed herein, a reference to a Cartesian plane or coordinate may be made in relation to FIG. 1A. One of ordinary skill will recognize that the particular choice of coordinate axes in FIG. 1A is not limiting of embodiments as disclosed herein. The choice of coordinate axes is done for illustration purposes only.

Figure 1B:
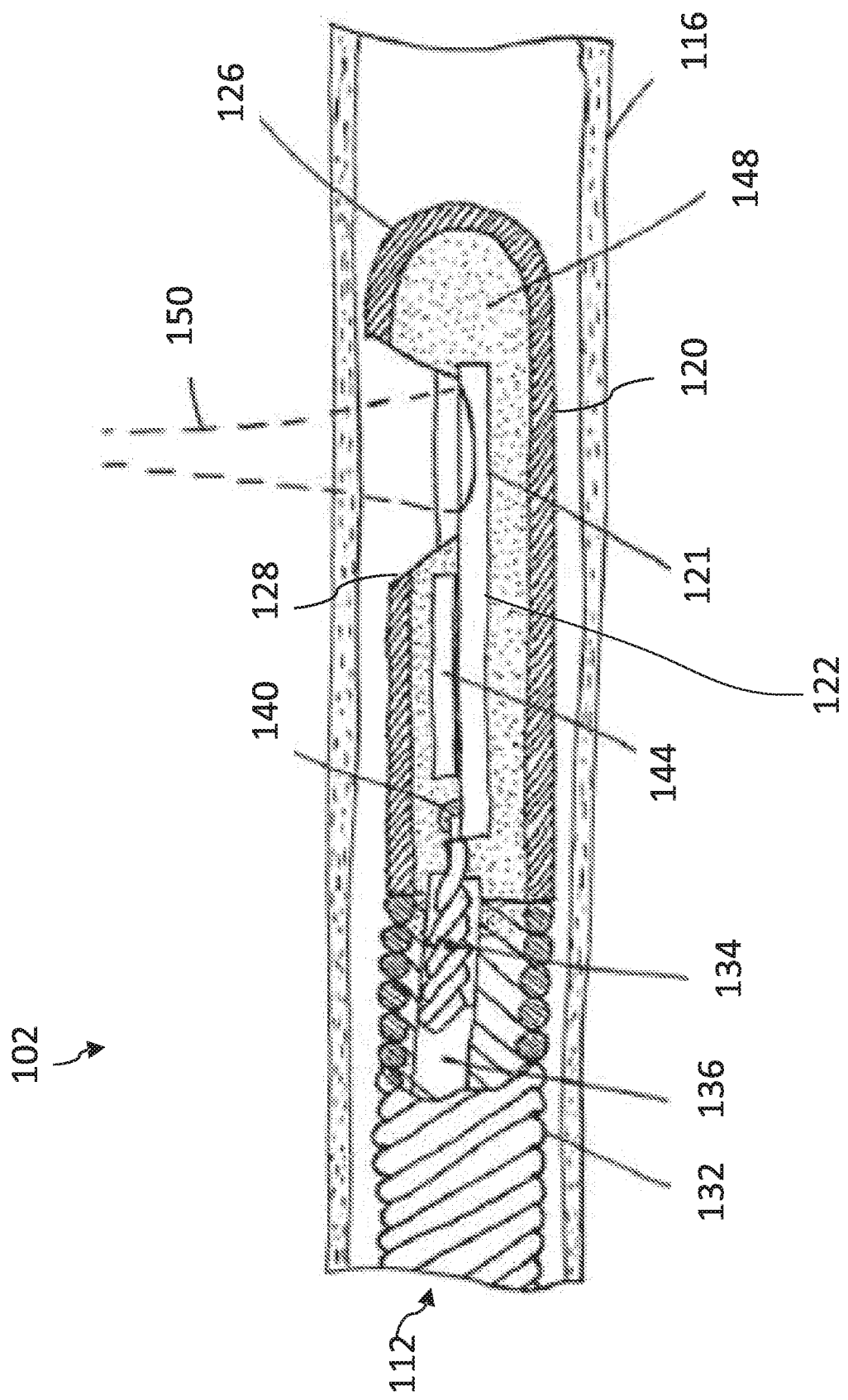
FIG. 1B is a cross-sectional side view of a distal portion of a catheter used in an IVUS imaging system, according to some embodiments.

FIG. 1B is a cross-sectional side view of a distal portion of a catheter used in an IVUS imaging system, according to some embodiments. In particular, FIG. 1B shows an expanded view of aspects of the distal portion of imaging core 112. In this exemplary embodiment, imaging core 112 is terminated at its distal tip by a housing 126 having a rounded nose and a cutout 128 for the ultrasound beam 150 to emerge from the housing. In some embodiments, a flexible driveshaft 132 of imaging core 112 is composed of two or more layers of counter wound stainless steel wires, welded, or otherwise secured to housing 126 such that rotation of the flexible driveshaft also imparts rotation to housing 126. In the illustrated embodiment, a PMUT MEMS transducer layer 121 includes a spherically focused portion facing cutout 128. In some embodiments, transducer assembly 122 may include application-specific integrated circuit (ASIC) 144 within distal portion 120 of imaging core 112. ASIC 144 is electrically coupled to transducer layer 221 through two or more connections. In that regard, in some embodiments of the present disclosure ASIC 144 may include an amplifier, a transmitter, and a protection circuit associated with PMUT MEMS layer 121. In some embodiments, ASIC 144 is flip-chip mounted to a substrate of the PMUT MEMS layer 121 using anisotropic conductive adhesive or suitable alternative chip-to-chip bonding method. When assembled together PMUT MEMS layer 121 and ASIC 144 form an ASIC/MEMS hybrid transducer assembly 122 mounted within housing 126. An electrical cable 134 with optional shield 136 may be attached to transducer assembly 122 with solder 140. Electrical cable 134 may extend through an inner lumen of the flexible driveshaft 132 to proximal end 118 of imaging core 112. In proximal end 118, cable 134 is terminated to an electrical connector portion of a rotational interface coupling catheter 102 to PIM 104 (cf. FIG. 1A). In the illustrated embodiment, transducer assembly 122 is secured in place relative to the housing 126 by an epoxy 148 or other bonding agent. Epoxy 148 may serve as an acoustic backing material to absorb acoustic reverberations propagating within housing 126 and as a strain relief for the electrical cable 134 where it is soldered to transducer assembly 122.

Figure 2A:
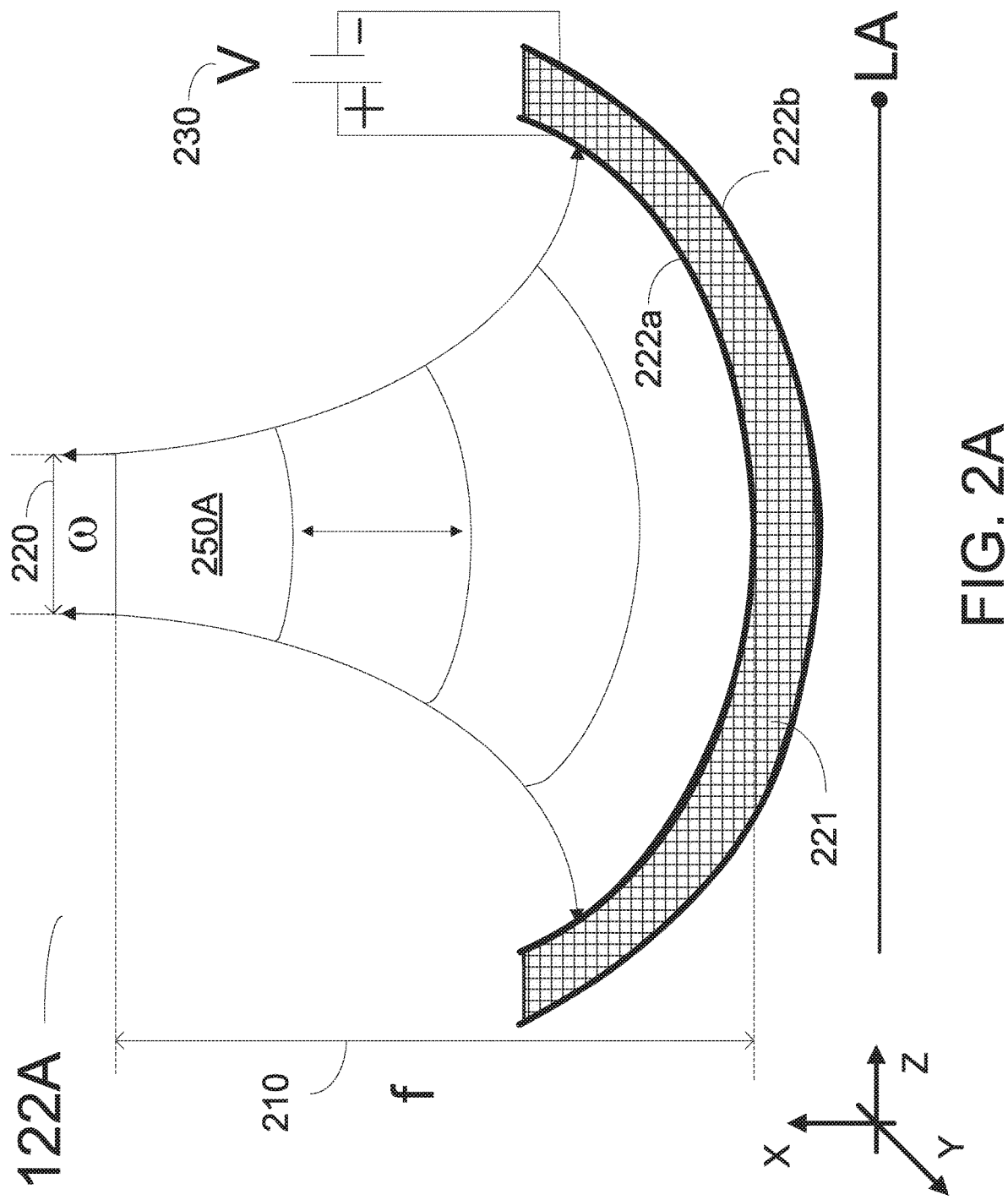
FIG. 2A is a partial illustration of a focusing transducer, according to some embodiments.

FIG. 2A is a partial illustration of a focusing transducer 122A, according to some embodiments. Transducer 122A includes a polymeric layer 221 having a first adjacent conductive layer 222a and a second adjacent conductive layer 222b. Polymeric layer 221 includes a piezo-electric polymer material made into a concave shape as depicted in FIG. 2A. In some embodiments, the polymer used in polymeric layer 221 may be a ferroelectric polymer such as polyvinylidene fluoride (PVDF). Further according to some embodiments, polymeric layer 221 may include PVDF-co-trifluoroethylene (PVDF-TrFE) as a piezo-electric material. A voltage 230 (V) is applied between conductive layers 222a and 222b in order to generate focused ultrasound beam 250A. Likewise, in some embodiments an incident ultrasound beam 250A may impinge on polymeric layer 221 and produce a deformation leading to a voltage difference V 230 between conductive layers 222a and 222b.

In some embodiments, the concavity of transducer 122A may be a section of a sphere. In some embodiments, the concavity of transducer 122A is directed radially outward, in a plane perpendicular to the LA (i.e., XY-plane in FIG. 2A). Accordingly, in rotational IVUS embodiments, transducer 122A rotates about the LA, thus sweeping focused beam 250A radially in the XY plane. In some embodiments, while transducer 122A may include a planar polymeric layer, an acoustic 'lens' may be placed adjacent to transducer 122A. Thus, focused acoustic beam 250A may be generated by acoustic wave refraction. Still further, the material forming sheath 110 may have an acoustic impedance, thereby focusing the acoustic wave propagating through sheath 110.

Figure 2B:
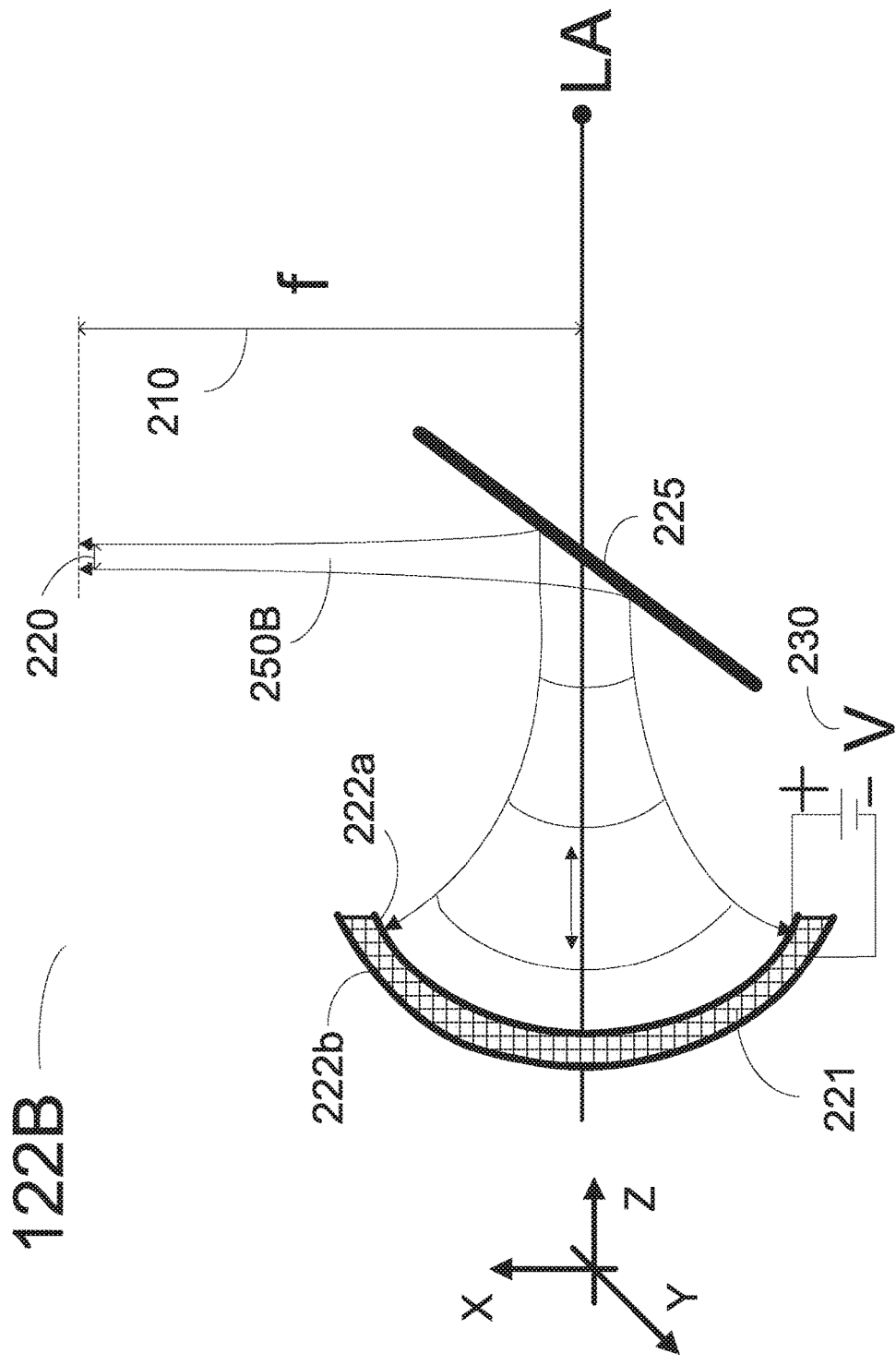
FIG. 2B is a partial illustration of a focusing transducer, according to some embodiments.

FIG. 2B is a partial illustration of a focusing transducer 122B, according to some embodiments. Transducer 122B may have a polymeric layer 221 with a concavity oriented along the LA. Focusing transducer 122B includes a rotating reflective element 225 to direct focusing ultrasonic beam 250B radially out of axial direction LA. According to some embodiments, focused ultrasonic beam 250B may be generated substantially along the blood vessel, or the LA axis. Then, beam 250B may be deflected radially outward by rotating reflective element 225, as shown in FIG. 2B.

Still further, the output of the transducer or a reflecting element may be oriented to generally align with the longitudinal axis LA. These devices may be swept through an arc to generate forward looking images.

Focused ultrasonic beams 250A, 250B have a focal distance 210 (f) converging into a focal waist 220 (ω). Accordingly, the focal waist has a diameter that may be less than 50 μm. Focal distance 210 is determined from the curvature of the surface formed by transducers 122A, 122B, and the refractive index of the propagation medium of focused acoustic beam 250. Typically, the propagation medium is blood, plasma, a saline solution, or some other bodily fluid. In some embodiments, focal distance 'f' may be as long as 10 mm, or more. Thus, the tissue penetration depth of focused ultrasonic beams 250A, 250B may be 5 mm, 10 mm, or more.

Focal distance 210 and focal waist 220 may also be determined by the curvature of the aperture. In some embodiments focused acoustic beam 250A, B may include a plurality of acoustic frequencies in a frequency bandwidth. The frequency bandwidth may be determined by the polymer material and the shape of polymeric layer 221. The structure of the transducer assembly including backing, electrodes, and matching layers may determine the acoustic frequency bandwidth of transducers 122A, 122B. The viscoelastic properties of the polymer material may also determine the acoustic frequency bandwidth of transducers 122A, 122B.

Accordingly, some embodiments have a polymeric layer 221 such that an ultrasonic signal produced by transducers 122A, 122B includes a frequency bandwidth from about 5 to about 135 Mega Hertz (MHz, 1 MHz=$10^6$ Hz). Embodiments of catheters 102 including a transducer such as transducers 122A, 122B allow for a better image resolution since ultrasonic beams 250A, 250B are focused.

Further according to some embodiments, the material and shape of distal portion 116 of sheath 110 may be selected to match the acoustic impedance of the materials in transducer 122 and the target structure (e.g., blood vessel wall). Impedance matching of the acoustic signal across all elements in the distal portion of catheter 102 is desirable to enhance the response of transducer 122 to the acoustic echo coming from the blood vessel wall. Embodiments of materials and shapes of distal portion 116 of sheath 110 to match the acoustic impedance in transducer 122 may be as disclosed in co-pending U.S. Patent Application entitled "Intravascular Ultrasound Catheter for Minimizing Image Distortion," U.S. Provisional App. No. 61/746,958, filed Dec. 28, 2012, hereby incorporated by reference in its entirety, for all purposes. Impedance matching layers can also be used to modify impedance match.

Figure 3:
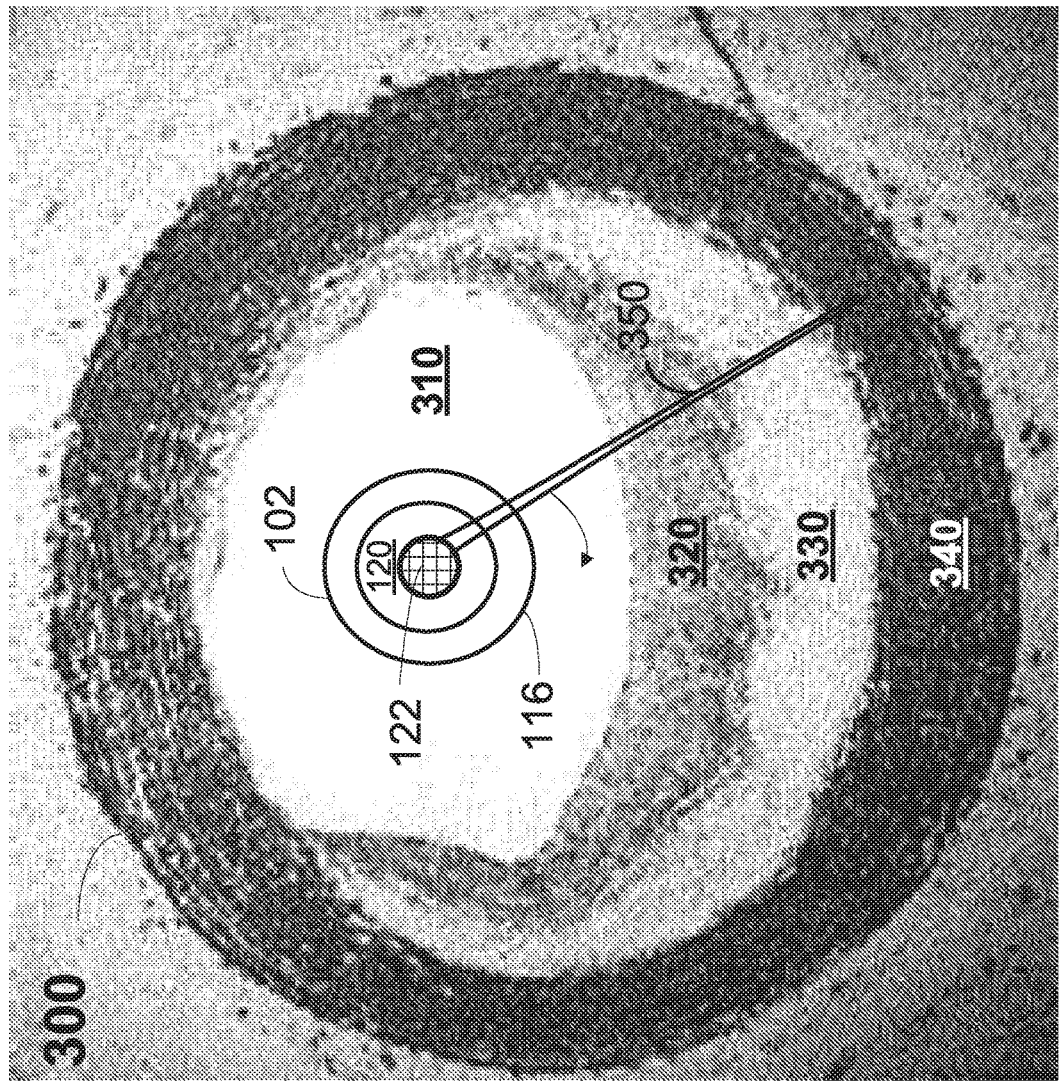
FIG. 3 is a cross-sectional illustration of an IVUS catheter inside a blood vessel, according to some embodiments.

FIG. 3 is a cross-sectional illustration of an IVUS catheter 102 inside a blood vessel 300, according to some embodiments. Blood vessel 300 includes a lumen 310, typically filled with a blood flow. FIG. 3 also shows a stenosed segment in blood vessel 300. The stenosis may include a plaque formed by a fibrous cap 320 adjacent to a necrotic core 330 formed in an interior side of a layer adventitia 340. Accordingly, methods for using an IVUS catheter in FACT enable the classification of a plaque in a stenosed segment of a blood vessel, such as illustrated in FIG. 3. For example, a plaque may be classified as 'vulnerable' to rupture, based on the size, configuration, and nature of its components. A component of a plaque within a vessel may be fibrous cap 320, and necrotic core 330. In some configurations a component of a plaque within a vessel may include fat cell tissue and macrophage cells. The nature of a component of a plaque within a vessel may include substances such as elastin, collagen and cholesterol. The viscoelastic properties of the substances and the configuration of the different components included in a plaque within a vessel provide a differentiated acoustic response. Thus, interaction with a focused ultrasound beam 350 may produce an image that clearly differentiates the components of the plaque, their nature, and their configuration (size and shape).

FIG. 3 depicts a focused ultrasonic beam 350 directed axially from catheter 102 toward the wall of blood vessel 300. Ultrasonic beam 350 is generated by transducer 122 inside distal end portion 120 of imaging core 112, and passes through distal end portion 116 of sheath 110 and blood plasma or a saline solution in lumen 310. According to some embodiments, focused ultrasonic beam 350 may be rotating about the LA of catheter 102, in a trajectory projected as a circle in the XY plane in FIG. 3.

In some embodiments, focused ultrasonic beam 350 may be reflected from the wall of blood vessel 300 towards transducer 122 in distal end portion 120 of imaging core 112. Thus, a reflected ultrasound signal may be recorded by PIM 104, providing information about the tissue in the wall of blood vessel 300. The reflected ultrasound signal may be the echo of a focused ultrasound signal projected onto the wall of blood vessel 300 from transducer 122 in the distal end 120 of imaging core 112. Beam 350 sweeps about the LA forming an arc, scanning a volume of the patient's tissue.

Figure 4:
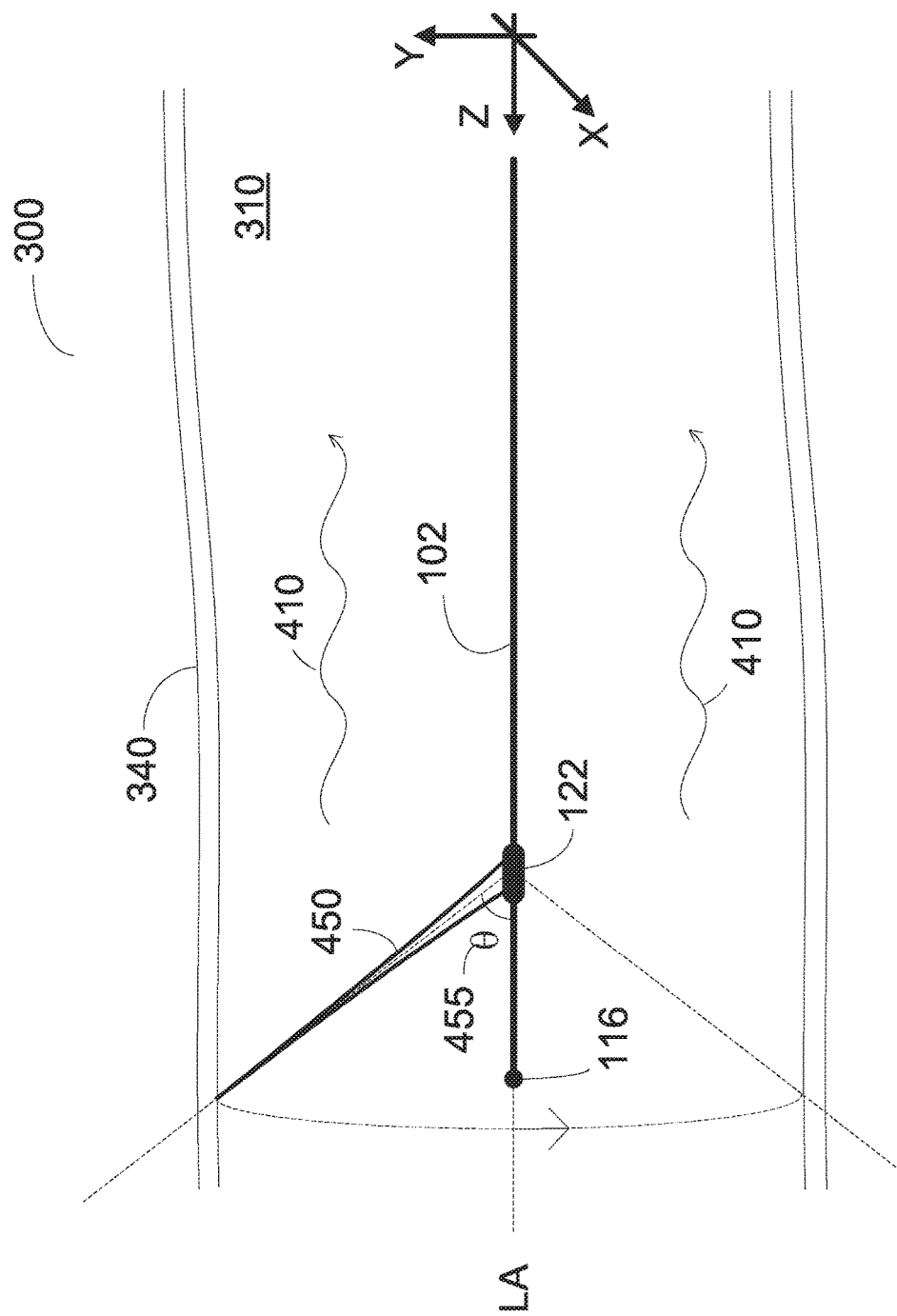
FIG. 4 is a longitudinal illustration of an IVUS catheter inside a blood vessel, according to some embodiments.

FIG. 4 is a longitudinal illustration of an IVUS catheter 102 inside a blood vessel 300, according to some embodiments. Focused ultrasound beam 450 is directed radially onto blood vessel wall 340 in a direction forming an azimuthal angle 455 (θ) with axis LA (along the Z-axis). Accordingly, angle 455 may have any value between zero (0°) and ninety (90°) degrees. In some embodiments, angle 455 may be larger than 90°, and close to 180°. FIG. 4 shows a blood 410 flowing in a direction substantially away from distal end 116 of catheter 102. In some embodiments, blood 410 may be flowing in a direction substantially away from a proximal end of catheter 102 (i.e., opposite of what is shown in FIG. 4). In general, blood flow is substantially parallel to the LA (Z-axis in FIG. 4), either along the +Z direction, or along the −Z direction.

In some embodiments as illustrated in FIG. 4, angle 455 may be 90° so that a transverse scan is obtained as focused ultrasound beam 450 is rotated about the LA. Thus, a transverse plane scan substantially parallel to the XY-plane may be obtained.

In some embodiments angle 455 is not perpendicular (90°) to the LA. For example, in some embodiments angle 455 may be less than 90° in a forward looking IVUS catheter. In configurations where angle 455 is not perpendicular, a component of the blood flow velocity along the direction of focused ultrasound beam 450 may be different from zero (0). When this is the case, an acoustic echo received from blood vessel wall 340 may be slightly shifted in frequency, by virtue of the Doppler effect. The frequency shift of the ultrasonic echo is related to the component of the flow velocity along the direction of focused ultrasound beam 450. For example, a frequency shift of the ultrasonic echo signal may be directly proportional to the magnitude of the component of the flow velocity along the direction of focused ultrasound beam 450. Thus, using knowledge of angle 455 and measuring the frequency shift of the echo signal, a blood flow speed may be obtained.

Figure 5:
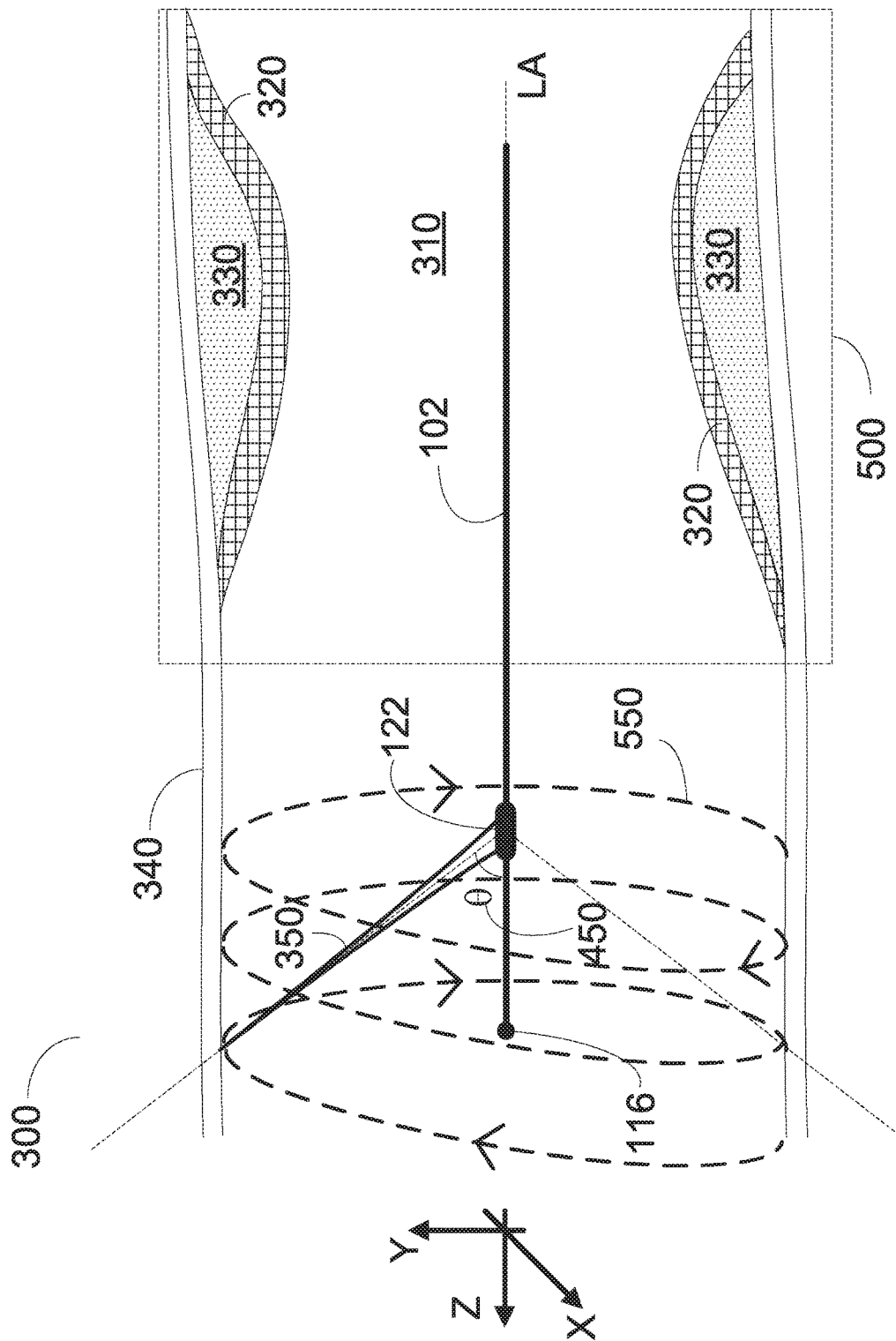
FIG. 5 is a longitudinal illustration of an IVUS catheter inside a blood vessel, according to some embodiments.

FIG. 5 is a longitudinal illustration of an IVUS catheter 102 inside a blood vessel 300, according to some embodiments. According to FIG. 5, IVUS catheter 102 axially advances along blood vessel 300. Blood vessel 300 may include a stenosed segment 500, having a plaque. The plaque within vessel 300 may include fibrous cap 320 on top of necrotic tissue 330. Blood vessel 300 also includes muscle cell tissue 340, as described in detail above (cf. FIGS. 3-4).

Focused ultrasound beam 350 forms a predetermined pattern 550 as it rotates around LA and catheter 102 is displaced in the +Z direction. For example, in some embodiments consistent with the present disclosure a predetermined pattern 550 may be a helicoid trajectory. In some embodiments, transducer 122 is retracted from, or pulled back through blood vessel 300. That is, distal end 116 is displaced in the −Z direction, according to some embodiments. Advancing and retracting transducer 122 along vessel 300 may be accomplished manually or with an automated system. Without limiting embodiments of the present disclosure, a retracted displacement (along the −Z direction) of transducer 122 will be assumed hereinafter.

As transducer 122 is retracted through the blood vessel 300, ultrasound echo signals collected along pattern 550 may be used to create an image of the blood vessel wall. The image of the blood vessel wall may be a 3D image including a plurality of cross sections of the blood vessel wall. The cross sections of the blood vessel wall may be substantially aligned with planes XY perpendicular to the Z-axis (i.e., the LA direction), along different points on the Z-axis. The image generated from pattern 550 may be processed by PIM 104 and control system 106 using an image characterization application, or code. The image characterization application may render a characterized tissue component map. In some embodiments, the image characterization application performs a spectral analysis of ultrasound echo information for a vessel cross-section. Thus, different plaque components may be determined and distinguished in the characterized tissue component map. For example, the characterization application may use a classification criterion including a rule based upon a location of a confluence of necrotic core 330 within the vessel cross-section in relation to a border between the lumen 310 and a plaque. A classification criterion may include a rule, based upon a location, in relation to a lumen-plaque border, of confluent necrotic core within the vessel cross-section; and rendering, in response to the classification, a plaque classification associated with the vessel cross-section. For example, a classification criterion may use the thickness of fibrous cap 320 to determine the vulnerability of a plaque, and the likelihood of plaque rupture and thrombosis.

Figure 6:
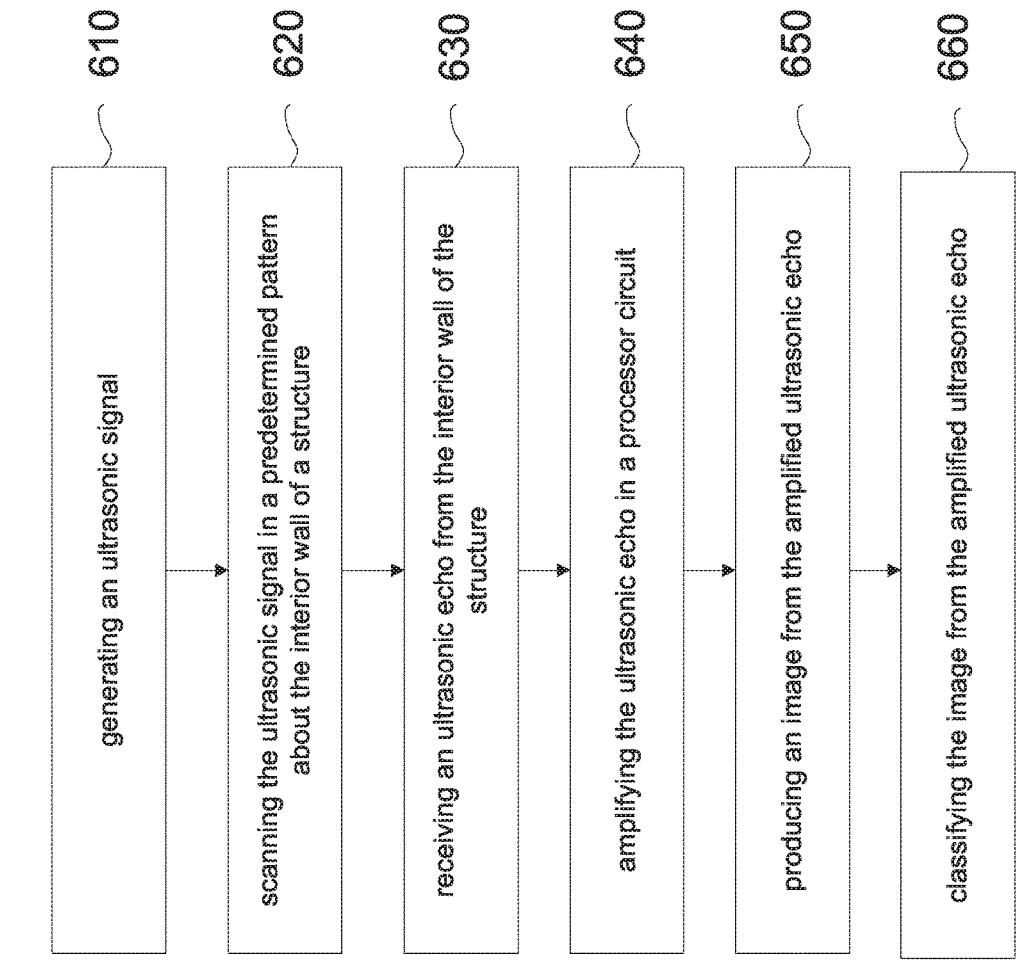
FIG. 6 is a flow chart illustrating steps in a method for focused acoustic computed tomography (FACT), according to some embodiments.

FIG. 6 is a flow chart illustrating steps in a method 600 for focus acoustic computed tomography (FACT), according to some embodiments. According to some embodiments, method 600 may be performed by control system 106 using processor circuit 156 and memory circuit 157 and/or PIM 104 using processor circuit 154 and memory circuit 155, based on scan data provided by transducer assembly 122 (cf. FIG. 1). Accordingly, some steps in method 600 may be performed by control system 106 and some steps in method 600 may be performed by PIM 104. A reconstructed image plane in method 600 may be provided to a user in display 108.

Step 610 includes generating an ultrasonic signal. In some embodiments, the ultrasonic signal may be generated from a transducer assembly (e.g., transducer assembly 122, cf. FIG. 1) in the form of an ultrasound acoustic beam following a path. The ultrasound acoustic beam path may be a focused path (e.g., focused acoustic beam 350, cf. FIG. 3) to produce a focal region of high acoustic intensity in a target portion of a tissue. Step 610 may include providing a voltage pulse to a transducer element (e.g., V 230, cf. FIGS. 2A, B). Accordingly, voltage pulse V 230 may be provided by PIM 104 to transducers 122A, B for a pre-selected period of time in step 610. Furthermore, voltage pulse V 230 may be provided in a series of pulses produced at a preselected frequency, in step 610.

Step 620 includes scanning the ultrasonic signal in a predetermined pattern about the interior wall of a structure. In some embodiments, step 620 may include sweeping the ultrasonic signal continuously in a predetermined pattern about the interior vessel wall. According to some embodiments, the sweeping is accomplished by rotating the transducer or a reflective surface which deflects the signal from the transducer within a catheter. The catheter may remain substantially stationary while the transducer is rotated and the acoustic signal is swept around the LA of the catheter. In some embodiments, the transducer is moved longitudinally, as it rotates about the LA to create a helical pattern (e.g., pattern 550, FIG. 5). In some embodiments, step 620 may be performed manually by an operator, or automatically through a motor included in PIM 104.

Step 630 includes receiving an ultrasonic echo from the interior wall of the structure. According to some embodiments, step 630 may be performed using a transducer, such as transducers 122A, 122B described in detail above, in relation to FIGS. 2A and 2B. Thus, upon receiving the ultrasonic echo from the interior wall of the structure, a deformation induced in a piezo-electric material in the transducer may result in a voltage signal. The transducer may further be configured to couple the voltage signal out of a vessel region into a processor circuit, such as processor circuit 154 in PIM 104.

In some embodiments, step 630 may be performed during a period of time between two voltage pulses from step 610. Thus, according to some embodiments in step 610 a voltage signal travels from processor circuit 154 in PIM 104 into transducer assembly 122 along catheter 102 (cf. FIG. 1). Further according to some embodiments, in step 630 a voltage signal travels from transducer assembly 122 to processor circuit 154 in PIM 104. In some embodiments, step 630 may include selecting a frequency band from the voltage received in the PIM. Accordingly, the high-bandwidth of transducer 122 may enable the selection of different frequency bands within the response band of the transducer.

Selecting a specific frequency band enables PIM 104 to reconstruct images from selected portions of the tissue structure. For example, the focal distance of a focused acoustic beam may be selected by selecting a frequency band in the voltage received from the transducer in step 630. Thus, the penetration depth of the acoustic echo signal may be selected in PIM 104 by selecting the frequency band of receive amplifier 114 in step 630.

Step 640 includes amplifying the ultrasonic echo in a processor circuit. The processor circuit in step 640 may be as processor circuit 154 in PIM 104 (cf. FIG. 1). According to some embodiments, the processor circuit in step 640 may include an ASIC provided adjacent to the transducer, in a distal portion of the catheter (e.g., ASIC 144, cf. FIG. 1B). Step 650 includes producing an image from the ultrasonic echo. According to some embodiments, step 650 may be performed partially by PIM 104. In some embodiments, step 650 may be performed partially by control system 106. According to some embodiments, step 650 includes producing a 2-dimensional image (2D-image) of a cross section of the blood vessel wall. The cross-section may be substantially parallel to an XY-plane perpendicular to a LA oriented along the blood vessel. In some embodiments, step 650 includes producing a 3-dimensional image (3D-image) of the blood vessel wall from a plurality of 2D-images. According to embodiments as described herein, step 650 may include forming an image with axial resolution better than 50 μm.

In some embodiments, step 650 may include complementing the image obtained from the IVUS catheter with an image obtained using an optical beam scanning technique, such as optical coherence tomography (OCT). For example, using an OCT system a high resolution image of a deep tissue structure may be obtained. Such a deep tissue image may be complemented with an IVUS image of tissue portions close to the catheter, including blood stream in a blood vessel.

Step 660 includes classifying the image from the ultrasonic echo. Step 660 may be performed by processor circuit 156 and memory circuit 157 in control system 106. In some embodiments, step 660 is performed by processor circuit 156 executing commands, retrieving and storing data, the commands and the data being stored in memory circuit 157. For example, in some embodiments the commands executed by processor circuit 156 in control system 106 may be included in an image characterization application stored in memory circuit 157. The image characterization application may be as described in detail above, in relation to FIG. 5. Image characterization applications as used in step 660 may be as disclosed in U.S. Pat. No. 7,627,156 entitled "Automated lesion analysis based upon automatic plaque characterization according to a classification criterion," U.S. Pat. No. 7,175,597 entitled "Non-Invasive Tissue Characterization System and Method," and U.S. Pat. No. 6,200,268 entitled "Vascular Plaque Characterization," each incorporated herein by reference in its entirety, for all purposes.

Figure 7:
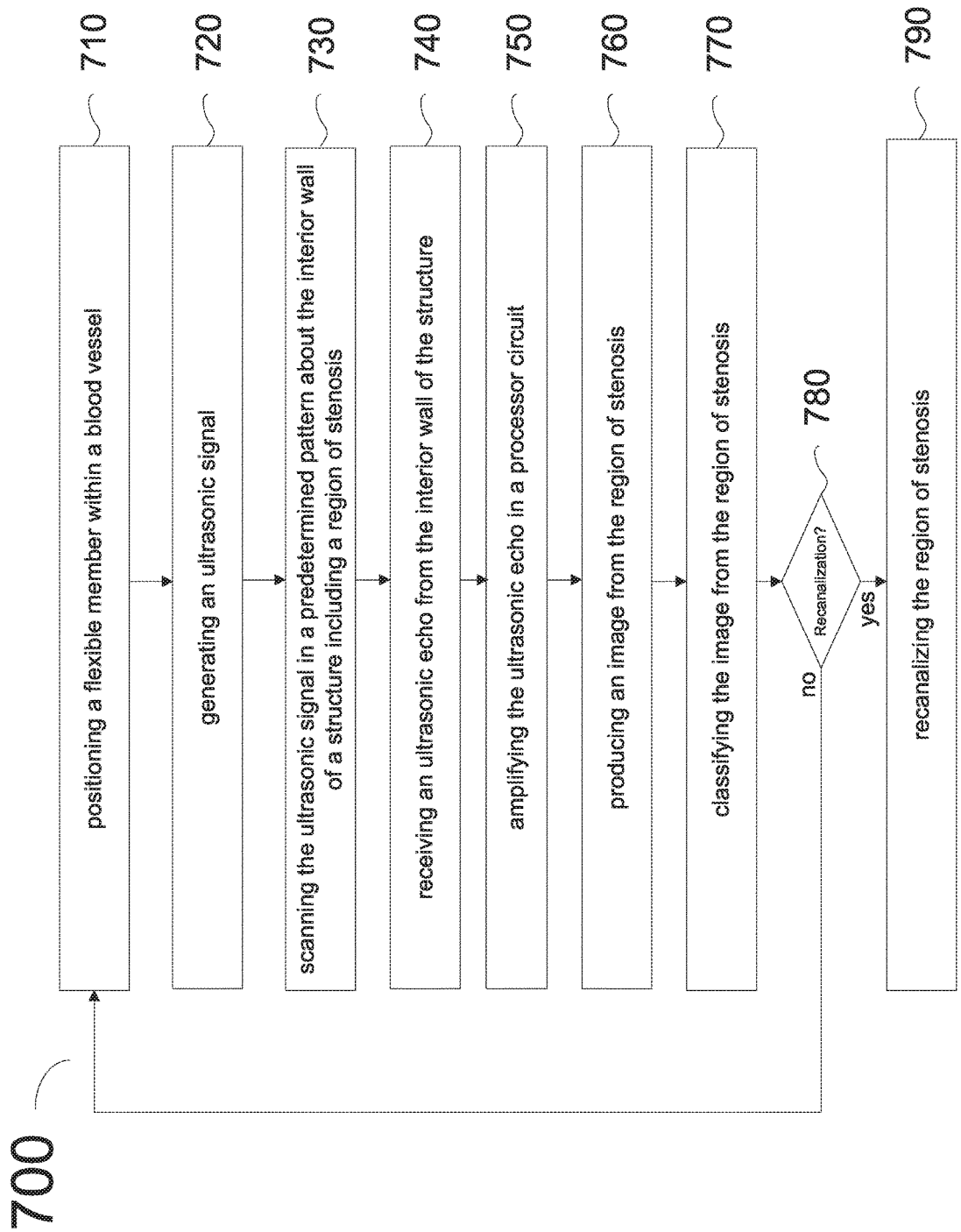
FIG. 7 is a flow chart illustrating steps in a method for recanalization of a blood vessel using FACT, according to some embodiments.

FIG. 7 is a flow chart illustrating steps in a method 700 for recanalization of a blood vessel using FACT, according to some embodiments. According to some embodiments, method 700 may be performed partially by system 100 and an external operator handling a recanalization tool. Steps performed by system 100 may be partially executed by control system 106 using processor circuit 156 and memory circuit 157. In some embodiments, steps performed by system 100 may be partially executed by PIM 104 using processor circuit 154 and memory circuit 155 based on scan data provided by transducer assembly 122 (cf. FIG. 1). A reconstructed image plane in method 700 may be provided to the external operator in display 108. Thus, the external operator makes a decision of whether or not to excise a portion of the stenosed segment of the blood vessel using a recanalization tool based on the reconstructed image plane on display 108. According to some embodiments the recanalization tool may be a physical instrument having a sharp end on an abrasive surface. In some embodiments, the recanalization tool may be a laser beam susceptible of being directed to a point in the blood vessel and ablate a tissue portion.

Step 710 includes positioning a flexible member within a blood vessel. A flexible member in step 710 may be as catheter 102, including a rotating imaging core 112 and a sheath 110. Step 710 may further include positioning catheter 102 with its LA substantially aligned with the blood vessel, inside the lumen portion of the blood vessel. Step 720 includes generating an ultrasonic signal. Step 720 may be as step 610, described in detail above in relation to method 600. Step 730 includes scanning the ultrasonic signal in a predetermined pattern about the interior wall of a structure including a region of stenosis. In some embodiments, the predetermined pattern may be as pattern 550 described in detail above (cf. FIG. 5). The region of stenosis may also be as stenosed segment 500, described in detail above (cf. FIG. 5).

Step 740 includes receiving an ultrasonic echo from the interior wall of the structure. Accordingly, step 740 may be as step 630 described in detail above, in relation to method 600. Step 750 includes amplifying the ultrasonic echo in a processor circuit. Step 750 may be as step 640 described in detail above, in relation to method 600. Step 760 includes producing an image from the region of stenosis, and may be as step 650 described in detail above in relation to method 600. Step 770 includes classifying the image from the region of stenosis, and may be as step 660 described in detail above in relation to method 600.

Step 780 includes querying whether or not the region of stenosis needs a recanalization procedure. A decision in step 780 may be made according to the detected vulnerability of a plaque that may be present in the region of stenosis. For example, when an image from the region of stenosis is classified as 'vulnerable plaque' in step 770, a recanalization may be recommended in step 780. When an image from the region of stenosis is classified in a category other than 'vulnerable plaque,' method 700 may be repeated from step 710. Thus, catheter 102 may be re-positioned at a different point along the blood vessel.

Step 790 includes recanalizing the region of stenosis. According to some embodiments, step 790 may be performed prior to steps 720 through 760. In some embodiments, step 790 may be performed after steps 720 through 760. Further according to some embodiments, step 790 may be performed at any point during execution of any one of steps 720 through 760. In some embodiments step 790 may include providing heat to a target region (e.g., stenosed segment 500, cf. FIG. 5) to mitigate the stenosis. In some embodiments, step 790 may include ablation, use of an abrasive surface, drug delivery, stenting, and drilling, to remove the stenosis. For example, step 790 may include lightly rubbing an abrasive surface against the tissue to remove a stenosed segment.

Embodiments of the invention described above are exemplary only. One skilled in the art may recognize various alternative embodiments from those specifically disclosed. Those alternative embodiments are also intended to be within the scope of this disclosure. As such, the invention is limited only by the following claims.

What is claimed is:

1. An intravascular ultrasound (IVUS) imaging system, comprising:
a catheter comprising a proximal portion, a distal portion, and an IVUS transducer disposed at the distal portion, wherein the distal portion is configured to be positioned within a blood vessel comprising a plurality of anatomical layers each located at a different depth, wherein the IVUS transducer is configured to:
emit an ultrasonic signal comprising a band of transmitted frequencies into the plurality of anatomical layers; and
receive an ultrasonic echo in response to the emitted ultrasonic signal;
a first processor in communication with the IVUS transducer and configured to:
receive an electrical signal representative of the ultrasonic echo;
select a band of frequencies of the ultrasonic echo, wherein the selected band of frequencies is within a response band of the IVUS transducer, wherein the response band of the IVUS transducer is within the band of transmitted frequencies, and wherein the selected band of frequencies corresponds to a desired imaging depth;
amplify the received electrical signal such that the ultrasonic echo is amplified in the selected band of frequencies; and
a second processor separate from the first processor, wherein the first processor is communicatively positioned between the IVUS transducer and the second processor, and wherein the second processor is configured to generate an IVUS image at the desired imaging depth based on the amplified ultrasonic echo in the selected band of frequencies.

2. The system of claim 1, wherein the catheter further comprises an application specific integrated circuit (ASIC) in communication with the IVUS transducer.

3. The system of claim 2, wherein the ASIC is positioned at the distal portion of the catheter.

4. The system of claim 1, wherein the IVUS transducer comprises a piezoelectric transducer or a capacitive transducer.

5. The system of claim 1, wherein the band of transmitted frequencies comprises a range from 5 MHz to 135 MHz.

6. The system of claim 1, wherein the IVUS transducer is configured to emit the ultrasonic signal in a predetermined pattern within the blood vessel.

7. The system of claim 6, wherein the predetermined pattern comprises a helical pattern.

8. The system of claim 1, wherein the catheter further comprises a rotating core configured to rotate IVUS transducer.

9. The system of claim 1, wherein the IVUS transducer comprises an array of elements.

10. The system of claim 1, wherein the second processor is further configured to:
classify the plurality of anatomical layers.

11. The system of claim 1, wherein the ultrasonic signal is directed at an oblique angle with respect to a longitudinal axis of the catheter.

12. The system of claim 1, wherein the IVUS transducer is configured to be displaced along a longitudinal axis of the blood vessel, and wherein the second processor is configured to generate a plurality of IVUS images along the longitudinal axis.

13. The system of claim 1, further comprising:
an interface module comprising the first processor; and
a control system comprising the second processor.

14. The system of claim 1, wherein the second processor is further configured to classify an anatomical layer of the blood vessel as a type of structure using the IVUS image based on the amplified ultrasonic echo in the selected band of frequencies.

* * * * *